US012290068B2

(12) United States Patent
Mechrez et al.

(10) Patent No.: US 12,290,068 B2
(45) Date of Patent: May 6, 2025

(54) SINGLE CELL ENCAPSULATION VIA PICKERING EMULSION FOR BIO-PESTICIDES APPLICATION

(71) Applicant: The State of Israel, Ministry of Agriculture & Rural Development Agricultural Research Organization (ARO), Rishon Lezion (IL)

(72) Inventors: Guy Mechrez, Rishon Lezion (IL); Dana Ment, Rishon Lezion (IL)

(73) Assignee: The State of Israel, Ministry of Agriculture & Rural Development Agricultural Research Organization, Rishon Lezion (IL)

( * ) Notice: Subject to any disclaimer, the term of this patent is extended or adjusted under 35 U.S.C. 154(b) by 865 days.

(21) Appl. No.: 17/059,233

(22) PCT Filed: May 27, 2019

(86) PCT No.: PCT/IB2019/054370
§ 371 (c)(1),
(2) Date: Nov. 26, 2020

(87) PCT Pub. No.: WO2019/229624
PCT Pub. Date: Dec. 5, 2019

(65) Prior Publication Data

US 2021/0212317 A1 Jul. 15, 2021

Related U.S. Application Data

(60) Provisional application No. 62/676,984, filed on May 27, 2018.

(51) Int. Cl.
*A01N 25/28* (2006.01)
*C12N 11/04* (2006.01)
*C12N 11/14* (2006.01)

(52) U.S. Cl.
CPC .............. *A01N 25/28* (2013.01); *C12N 11/04* (2013.01); *C12N 11/14* (2013.01)

(58) Field of Classification Search
None
See application file for complete search history.

(56) References Cited

U.S. PATENT DOCUMENTS

| | | | | |
|---|---|---|---|---|
| 6,180,141 B1 | 1/2001 | Lemercier et al. | | |
| 2007/0280981 A1 | 12/2007 | Birthisel | | |
| 2015/0125498 A1* | 5/2015 | Dejmek | .................... | A23L 5/40 426/654 |

FOREIGN PATENT DOCUMENTS

| | | | |
|---|---|---|---|
| WO | 2014106208 A1 | 7/2014 | |

OTHER PUBLICATIONS

Mao, A.S., et al., Deterministic encapsulation of single cells in thin tunable microgels for niche modelling and therapeutic delivery, Nature Materials 16, 236-243 (2017) (Year: 2017).*
Bashir, O., et al., Controlled-release of Bacillus thuringiensis formulations encapsulated in light resistant colloidosomal microcapsules for the management of lepidopteran pests of Brassica crops PeerJ 4:e2524; DOI 10.7717/peerj.2524 (Year: 2016).*
Ment, D., Resistant ticks inhibit Metarhizium infection prior to haemocoel invasion by reducing fungal viability on the cuticle surface, Environmental Microbiology (2012) doi: 10.1111/j.1462-2920.2012.02747.x (Year: 2012).*
Pan, M., et al., Fluorinated Pickering Emulsions Impede Interfacial Transport and Form Rigid Interface for the Growth of Anchorage-Dependent Cells, ACS Appl. Mater. Interfaces 2014, 6, 21446-21453 (Year: 2014).*
Mao A. S. et al. "Deterministic encapsulation of single cells in thin tunable microgels for niche modelling and therapeutic delivery" Nature materials. Feb. 28, 2017;16(2):236.
Masuda M. "Microencapsulation of Pesticides for Controlling Release from Coatings" Chalmers University of Technology; Dec. 31, 2011.
Yaakov N. et al., "Single Cell Encapsulation via Pickering Emulsion for Biopesticide Applications" ACS omega. Oct. 29, 2018;3(10):14294-301.
Bashir O. et al, "Controlled-release of Bacillus thurigiensis formulatimis encapsulated in light-resistant calloidosomal microcapsules for the management of lepidopteran pests of Brassioa crops" PEERJ, vol. 4, No. e2524. Oct. 11, 2016 (Oct. 11, 2016).
Van Wijk J. et al., "Compartmentalization of bacteria in microcapsules" Chemical Communications, vol. 50, No. 97, Jan. 1, 2014.
Kamanina O. et al., "Silica sol-gel encapsulated methylotrophic yeast as filling of biofilters for the removal of methanol from industrial wastewater" Enzyme and Microbial Technology, Stoneham, MA, US, vol. 92, Jul. 6, 2016.
Wang, P., Lombi, E., Zhao, F., & Kopittke, P. M. (2016). Nanotechnology: A New Opportunity in Plant Sciences. Trends in Plant Science, 21(8), 699-712. https://doi.org/10.1016/j.tplants.2016.04.005.
F.R.S. Paixão, E.R. Muniz, L.P. Barreto, C.C. Bernardo, G.M. Mascarin, C. Luz & É.K.K. Fernandes (2017): Increased heat tolerance afforded by oil-based conidial formulations of Metarhizium anisopliae and M. robertsil, Biocontrol Science and Technology, DOI: 10.1080/09583157.2017.1281380.
He, M., Edgar, J. S., Jeffries, G. D. M., Lorenz, R. M., Shelby, J. P., & Chiu, D. T. (2005). Selective Encapsulation of Single Cells and Subcellular Organelles into Picoliter-and Femtoliter-Volume Droplets. Analytical Chemistry, 77(6), 1539-1544. doi:10.1021/ac0480850.
Supplementary European Search Report for EP 19810800 mailed on Jun. 28, 2021.
International Search Report for PCT/IB2019/054370 mailed on Sep. 16, 2019.

* cited by examiner

*Primary Examiner* — H. Sarah Park
(74) *Attorney, Agent, or Firm* — Rivka Friedman

(57) ABSTRACT

This invention provides a systems and methods for single cell microencapsulation by eco-friendly oil-in-water (o/w) Pickering emulsion.

7 Claims, 9 Drawing Sheets

SINGLE CELL ENCAPSULATION VIA PICKERING EMULSION FOR BIO-PESTICIDES APPLICATION

CROSS-REFERENCES TO RELATED APPLICATIONS

This application is related to and claims priority from commonly owned US Provisional patent applications: U.S. Provisional Patent Application Ser. No. 62/676,984, entitled: Single cell encapsulation via Pickering emulsion for biopesticides application, filed on May 27, 2018, the disclosure of which is incorporated by reference in its entirety herein.

TECHNICAL FIELD

The present invention relates to the field of Pickering emulsions and single cell encapsulation.

BACKGROUND OF THE INVENTION

Single cell encapsulation has many major applications in a wide variety of fields including medicine, food industry, and agriculture. Encapsulation protects against harsh external conditions, ensures lower exposure to contamination by foreign organisms, and provides improved isolation. Cell encapsulation has become an important tool in gene therapy, controlling drug delivery, fermentation industry, image analysis tool, and genomic analysis in microorganisms. Several techniques for single cell encapsulation have been developed, including solvent evaporation, interfacial polymerization, and layer-by-layer deposition. Nevertheless, these methods may contain toxic chemicals and compounds such as organic solvents or corrosive surfactants that constitute risks for biological organisms.

Pickering emulsions have been used for single cell encapsulation, given their high colloidal stability and controllable droplet size. Pickering emulsions are stabilized by nanoparticles (NPs) that are self-assembled at the oil/water interface and act as a physical barrier. Pickering emulsions are in the form of oil-in-water (o/w) or inverse (water-in-oil) emulsions. Cell encapsulation by Pickering emulsions has become useful for various applications, such as encapsulation of microbial cells to protect from pH changes, developing bio-pesticide formulations based on *Bacillus thuringiensis* (Bt), platform for enzymatic reaction, cellular capsules based on liquid marbles, and encapsulation of adherent cells in water-in-water emulsions for tissue engineering

SUMMARY OF THE INVENTION

The present invention provides a system and method for single cell microencapsulation by eco-friendly oil-in-water (o/w) Pickering emulsion.

Embodiments of the invention are directed to a method for single cell encapsulation. The method comprises: providing a water-based solution including nanoparticles, emulsifying the water-based solution by adding an oil solution into the water-based solution, providing cells into the solution and generating at least one single cell encapsulation of the cells.

Optionally, the method is such that, the nanoparticles are silica nanoparticles.

Optionally, the method is such that, the nanoparticles are Titania nanoparticles.

Optionally, the method is such that, the nanoparticles are either organic or inorganic nanoparticles.

Optionally, the method is such that, the nanoparticles introduce functionalized groups.

Optionally, the method is such that, the functionalized groups are one of: amine group, Acryloxymethyltrimethoxysilane, (3-acryloxypropyl)trimethoxysilane, 3-aminopropyltrimethoxysilane, 3-aminopropyltriethoxysilane, n-(2-aminoethyl)-3-aminopropyltrimethoxysilane, Ethyltrimethoxysilane, n-propyltriethoxysilane, Isobutyltriethoxysilane, Hexyltrimethoxysilane, Octyltrimethoxysilane, 4-Aminobutyltriethoxysilane, 3-Aminopropyldiisopropylethoxysilane, 3-Mercaptopropyltriethoxysilane, 3-Mercaptopropyltrimethoxysilane, 1-Mercaptoundecyltrimethoxysilane, S-(Octanoyl)Mercaptopropyltriethoxysilane, 1H,1H,2H,2H-Perfluorooctyltrimethoxysilane, (3,3,3-Trifluoropropyl)trimethoxysilane, n-Octylmethyldiethoxysilane, (3,3,3-trifluoropropyl)trimethoxysilane, Undecyltrichlorosilane, Dodecyltriethoxysilane, Docosyltriethoxysilane, Dimethyldimethoxysilane, Dimethyldichlorosilane, n-Butyltriethoxysilane, (3-glycidyloxypropyl)trimethoxysilane, 2-(3,4-epoxycyclohexyl)ethyltrimethoxysilane, 3-isocyanatopropyltriethoxysilane, bis[3-(triethoxysilyl)propyl]tetrasulfide.

Optionally, the method is such that, the emulsifying is generated by ultrasonication.

Optionally, the method is such that, the oil-based solution is paraffin oil.

Optionally, the method is such that, the oil-based solution is one of: silicon oil, sunflower oil, mineral oil and other biocompatible and eco-friendly oil.

Optionally, the method is such that, the cells are *Metarhizium brunneum* Mb7 conidia.

Optionally, the method is such that, the cells are one of: bacteria, virus, yeast cell, conidia, spore of a fungus, a soil-inhabited entomopathogenic fungus (EPF), bacteria pathogenic to insect and a pesticide emitting composition.

Optionally, the method is such that, the spore of a fungus is one of: *Metarhizium anisopliae, Metarhizium brunneum, Metarhizium robertsii, Metarhizium frigidum, Metarhizium riley, Metarhizium acridum, Beauveria brongniartii, Beauveria bassiana, Veticillium lecanii, Isaria furnosoroseous*

Optionally, the method is such that, the at least one single cell encapsulation is generated by vortexing.

Optionally, the method is such that, the nanoparticles content is between 0.1 wt % to 10 wt %.

Optionally, the method is such that, the oil/water ratio is one of: 1:99, 5:95, 10:90, 20:80, 30:70, 40:60 and 50:50 respectively.

Optionally, the method is such that, the oil droplets can varied form 0.1-300 μm.

Embodiments of the invention are directed to a method for single cell encapsulation. The method comprises: providing a water-based solution including nanoparticles, emulsifying the water-based solution by adding an oil solution into the water-based solution, providing cells into the solution, generating at least one single cell encapsulation of the cells, and applying the at least one single cell encapsulation onto at least on leaf for pest control.

Optionally, the method is such that, the nanoparticles are silica nanoparticles.

Optionally, the method is such that, the nanoparticles introduce functionalized groups.

Optionally, the method is such that, the functionalized groups are one of: amine group, Acryloxymethyltrimethoxysilane, (3-acryloxypropyl)trimethoxysilane, 3-aminopropyltrimethoxysilane, 3-aminopropyltriethoxysilane, n-(2-aminoethyl)-3-aminopropyltrimethoxysilane, Ethyltrimethoxysilane, n-propyltriethoxysilane, Isobutyltriethoxysilane, Hexyltrimethoxysilane, Octyltrimethoxysilane, 4-Aminobutyltriethoxysilane, 3-Aminopropyldiisopropylethoxysilane, 3-Mercaptopropyltriethoxysilane, 3-Mercaptopropyltrimethoxysilane, 1-Mercaptoundecyltrimethoxysilane, S-(Octanoyl)Mercaptopropyltriethoxysilane, 1H,1H, 2H,2H-Perfluorooctyltrimethoxysilane, (3,3,3-Trifluoropropyl)trimethoxysilane, n-Octylmethyldiethoxysilane, (3,3,3-trifluoropropyl)trimethoxysilane, Undecyltrichlorosilane, Dodecyltriethoxysilane, Docosyltriethoxysilane, Dimethyldimethoxysilane, Dimethyldichlorosilane, n-Butyltriethoxysilane, (3-glycidyloxypropyl)trimethoxysilane, 2-(3, 4-epoxycyclohexyl)ethyltrimethoxysilane, 3-isocyanatopropyltriethoxysilane, bis[3-(triethoxysilyl)propyl]tetrasulfide.

Optionally, the method is such that, the emulsifying is generated by ultrasonication.

Optionally, the method is such that, the oil-based solution is paraffin oil.

Optionally, the method is such that, the cells are *Metarhizium brunneum* Mb7 conidia.

Optionally, the method is such that, the cells are one of: bacteria, virus, yeast cell, conidia, spore of a fungus, a soil-inhabited entomopathogenic fungus (EPF), bacteria pathogenic to insect and a pesticide emitting composition.

Optionally, the method is such that, the spore of a fungus is one of: *Metarhizium anisopliae, Metarhizium brunneum, Metarhizium robertsii, Metarhizium frigidum, Metarhizium riley, Metarhizium acridum, Beauveria brongniartii, Beauveria bassiana, Veticillium lecanii, Isaria fumosoroseous.*

Optionally, the method is such that, the at least one single cell encapsulation is generated by vortexing.

Optionally, the method is such that, the nanoparticles content is between 0.1 wt % to 10 wt %.

Optionally, the method is such that, the oil/water ratio is one of: 5:95, 10:90, 20:80 and 30:70 respectively.

Optionally, the method is such that, the at least on leaf is a *R. communis* leaf.

Optionally, the method is such that, the pests are one of: *Lepidoptera, Coleoptera, Hemiptera, Diptera, Orthoptera, Acari, Gastropoda*

Optionally, the method is such that, the pests are arthropod.

Optionally, the method is such that, the at least one single cell encapsulation create a silica-based honeycomb-like formation on the at least on leaf.

Optionally, the method is such that, the oil droplets can varied form 0.1-300 μm.

Embodiments of the invention are directed to a system for single cell encapsulation. the system comprises: An oil droplet, a plurality of nanoparticles around the periphery of the oil droplet, and a single cell particle within the oil droplet.

Optionally, the system is such that, the oil droplet is a paraffin oil droplet.

Optionally, the system is such that, the plurality of nanoparticles are silica nanoparticles.

Optionally, the system is such that, the plurality of nanoparticles introduce functionalized groups.

Optionally, the system is such that, the functionalized groups are one of: amine group, Acryloxymethyltrimethoxysilane, (3-acryloxypropyl)trimethoxysilane, 3-aminopropyltrimethoxysilane, 3-aminopropyltriethoxysilane, n-(2-aminoethyl)-3-aminopropyltrimethoxysilane, Ethyltrimethoxysilane, n-propyltriethoxysilane, Isobutyltriethoxysilane, Hexyltrimethoxysilane, Octyltrimethoxysilane, 4-Aminobutyltriethoxysilane, 3-Aminopropyldiisopropylethoxysilane, 3-Mercaptopropyltriethoxysilane, 3-Mercaptopropyltrimethoxysilane, 1-Mercaptoundecyltrimethoxysilane, S-(Octanoyl)Mercaptopropyltriethoxysilane, 1H,1H, 2H,2H-Perfluorooctyltrimethoxysilane, (3,3,3-Trifluoropropyl)trimethoxysilane, n-Octylmethyldiethoxysilane, (3,3,3-trifluoropropyl)trimethoxysilane, Undecyltrichlorosilane, Dodecyltriethoxysilane, Docosyltriethoxysilane, Dimethyldimethoxysilane, Dimethyldichlorosilane, n-Butyltriethoxysilane, (3-glycidyloxypropyl)trimethoxysilane, 2-(3, 4-epoxycyclohexyl)ethyltrimethoxysilane, 3-isocyanatopropyltriethoxysilane, bis[3-(triethoxysilyl)propyl]tetrasulfide.

Optionally, the system is such that, the single cell particle is *Metarhizium brunneum* Mb7 conidia conidium.

Unless otherwise defined herein, all technical and/or scientific terms used herein have the same meaning as commonly understood by one of ordinary skill in the art to which the invention pertains. Although methods and materials similar or equivalent to those described herein may be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the present invention are herein described, by way of example only, with reference to the accompanying drawings. With specific reference to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Attention is now directed to the drawings, where like reference numerals or characters indicate corresponding or like components. In the drawings.

Figure 6A:
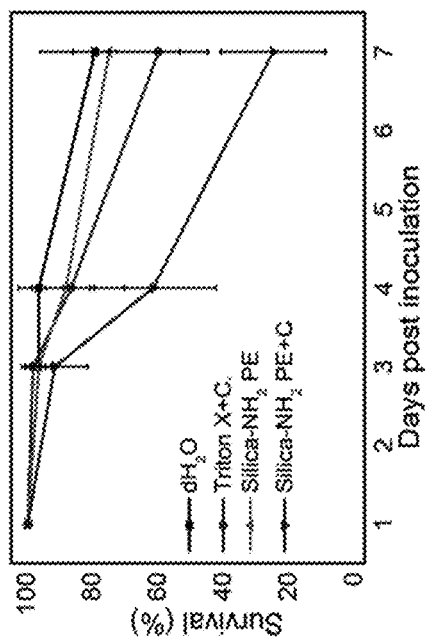
FIG. 6A is a survival curve graph of *S. littoralis* third-instar larvae after spray application of dH2O, 0.01% Triton X-100 with conidia, silica-NH2 Pickering emulsion with *M.*
Figure 6B:
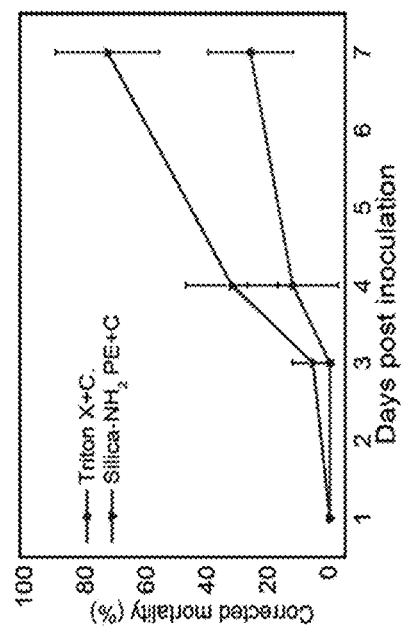
Figure 7:
Figure 7:
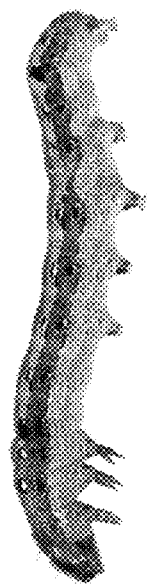

*brunneum* formulation, and silica-NH2 Pickering emulsion without *M. brunneum* formulation;

FIG. 6B is a corrected mortality % graph of *S. littoralis* larvae seven days post inoculation with *M. brunneum* conidia in a water based formulation (Triton X-100) and silica-NH2 Pickering emulsion;

FIG. 7A-B are images of *S. littoralis* third-instar larvae (A) treated with *M. brunneum* Pickering emulsion formulation 10 days post inoculation and (B) untreated larva;

DESCRIPTION OF THE PREFERRED EMBODIMENTS

The present invention is not limited in its application to the details of construction and the arrangement of the components set forth in the following description. The invention is capable of other embodiments, or of being practiced or carried out in various ways. Also, it is to be understood that the phraseology and terminology employed herein is for the purpose of description and should not be regarded as limiting.

Figure 1:
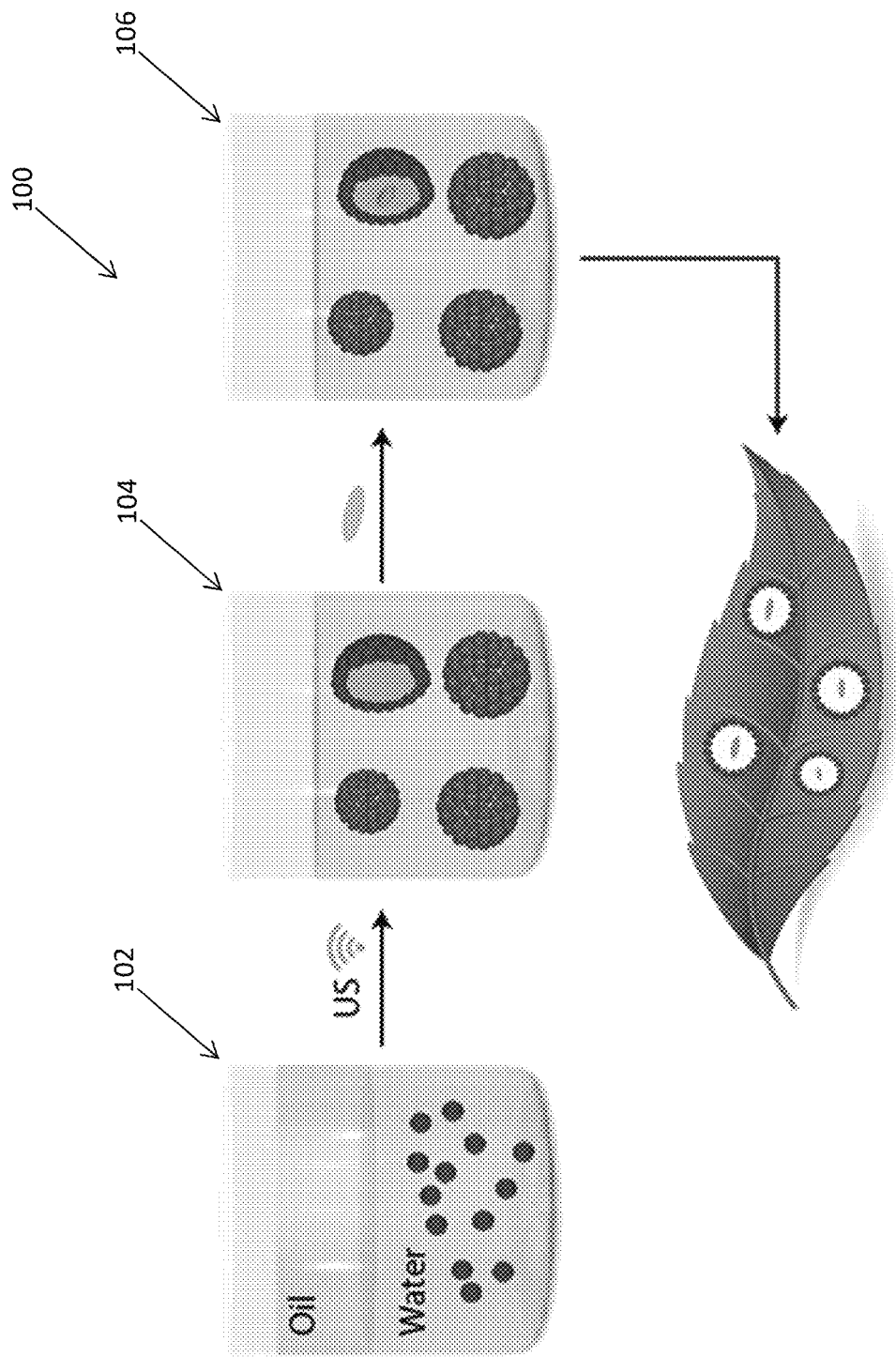
FIG. 1 is a schematic illustration of the system and method according to an embodiment of the present invention.

FIG. 1 is a schematic illustration of the system and method 100 of an example embodiment of the invention. Initially, nanoparticles including functionalized groups, for example, silica nanoparticles functionalized by, for example, (3-aminopropyl) triethoxysilane (APTES) through salinization to introduce amine-functionalized groups, are added into a water solution in the vessel 102. The vessel 102 is, for example, a standard reaction vessel. The added nanoparticles are dispersed in the water solution by, for example, Ultra-sonication. Ultra-sonication is provided by, for example, an ultrasonic liquid processor, such as Sonics Vibra-cell ultrasonic liquid processor, Model-VCX 750. The nanoparticles can be either organic or inorganic nanoparticles.

The functionalized groups introduced on nanoparticles may also be, for example, Acryloxymethyltrimethoxysilane, (3-acryloxypropyl) trimethoxysilane, 3-aminopropyltrimethoxysilane, 3-aminopropyltriethoxysilane, n-(2-aminoethyl)-3-aminopropyltrimethoxysilane, Ethyltrimethoxysilane, n-propyltriethoxysilane, Isobutyltriethoxysilane, Hexyltrimethoxysilane, Octyltrimethoxysilane, 4-Aminobutyltriethoxysilane, 3-Aminopropyldiisopropylethoxysilane, 3-Mercaptopropyltriethoxysilane, 3-Mercaptopropyltrimethoxysilane, 1-Mercaptoundecyltrimethoxysilane, S-(Octanoyl) Mercaptopropyltriethoxysilane, 1H,1H,2H,2H-Perfluorooctyltrimethoxysilane, (3,3,3-Trifluoropropyl) trimethoxysilane, n-Octylmethyldiethoxysilane, (3,3,3-trifluoropropyl) trimethoxysilane, Undecyltrichlorosilane, Dodecyltriethoxysilane, Docosyltriethoxysilane, Dimethyldimethoxysilane, Dimethyldichlorosilane, n-Butyltriethoxysilane, (3-glycidyloxypropyl) trimethoxysilane, 2-(3,4-epoxycyclohexyl) ethyltrimethoxysilane, 3-isocyanatopropyltriethoxysilane, bis[3-(triethoxysilyl)propyl]tetrasulfide and the like.

At a second stage, an oil solution, for example, a paraffin oil solution is added into the vessel 102 to form silica-NH2 Pickering emulsion. The oil solution can also be: silicon oil, sunflower oil, mineral oil and other biocompatible, eco-friendly oil and the like. Ultra-sonication is applied after the addition of the oil solution in order to generate emulsification. During this stage, the nanoparticles are assembled on the surface of the Pickering emulsions, as shown in the vessel 104. The exposure of the liquid sample to ultrasonic waves results in agitation, such that shear forces are responsible for the emulsification. In addition, the ultrasonic waves cause temporary voids at the interface of the Pickering emulsions, allowing particles to penetrate the Pickering emulsions. The silica nanoparticles content may vary, for example from 0.1 wt % to 10 wt %, while the oil/water ratio can be, for example, 20:80, 30:70, etc.

At a third stage, single cell particles such as conidia e.g. *Metarhizium brunneum* Mb7 conidia are added into the mixture containing the Pickering emulsions. The mixture is then vortexed at high speed in vortex mixers for approximately 5 minutes. The agitation by vortex enables the penetration of the cells into the paraffin droplets. Each added single cell is absorbed by a paraffin droplet to create single cell encapsulation, as shown in the vessel 106.

The single cell encapsulations include an oil droplet surrounded peripherally by a plurality of nanoparticles, and a single cell particle located within the oil droplet.

The hydrophobic outer layer of the added single cell particles augments the attachment and germination process on the host surface, and is also responsible for the individual arrangement of the particle in the oil phase. The single cell particles are incorporated only after the emulsion formation, since Ultra-sonication in the presence of the single cell particles can lead to cell lysis, which is to be avoided.

The single cell particles may also be: virus, yeast cell, spore or conidia of a fungus (*Metarhizium anisopliae, Metarhizium brunneum, Metarhizium robertsii, Metarhizium frigidum, Metarhizium riley, Metarhizium acridum, Beauveria brongniartii, Beauveria bassiana, Veticillium lecanii, Isaria fumosoroseous* and the like), a soil-inhabited entomopathogenic fungus (EPF), bacteria pathogenic to insect, a pesticide emitting composition, and the like At a final stage, a bio-pesticide formulation including the Pickering emulsions is sprayed on a leaf or group of leaves, for example, *R. communis* leaves for arthropod pest control. After drying of the emulsion, a silica-based honeycomb-like structure with an ordered hierarchical porosity is formed. This structure preserves the basic morphology of the Pickering emulsion and the single cell encapsulation. This leads to a high distribution of the single cell particles on the leaves for wide and long-lasting protection. The pest is, for example, *Lepidoptera, Coleoptera, Hemiptera, Diptera, Orthoptera, Acari, Gastropoda* and the like, while the treated plant may also be: corn, wheat, oilseed rape, melon, tomato, alfalfa, sorghum, onion, citrus, bean, sugarcane, coffee, and the like.

While the aforementioned stages are provided above, the order thereof is exemplary, and other orders of these stages are also permissible. In addition, the aforementioned stages are also applicable for inverse (water-in-oil) emulsions where water droplets containing hydrophilic single cell particles are formed in an oil-based solution.

Figure 2A:
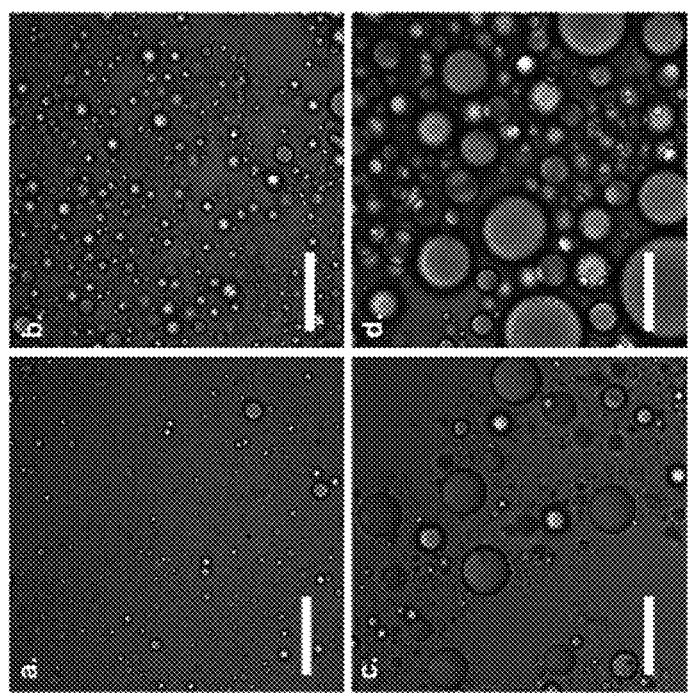
FIG. 2A are confocal microscopy images (a-d) illustrating Pickering emulsions with 1% silica-$NH_2$ at different oil/water ratios. (a) 5:95. (b) 10:90. (c) 20:80. (d) 30:70. The scale bar is 50 μm.
Figure 2B:
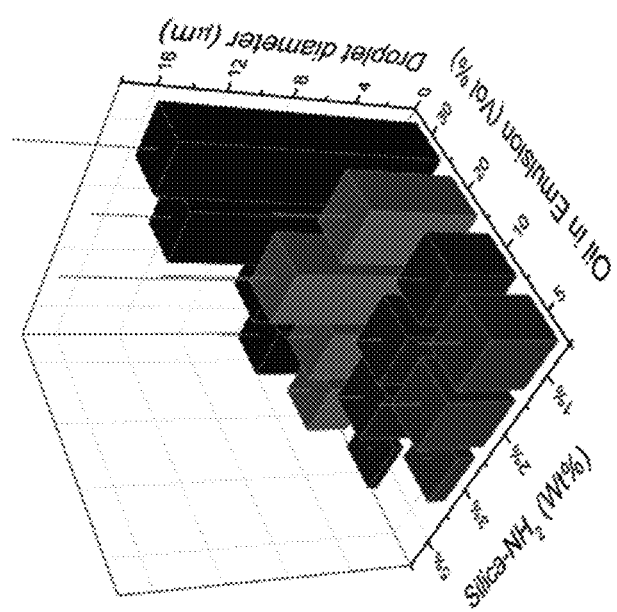
FIG. 2B is a column chart of Droplet diameter as a function of silica-NH2 contents (wt %) and oil percentages in the emulsion (vol %)

FIG. 2B is a column chart of Droplet diameter as a function of silica-NH2 contents (wt %) and oil percentages in the emulsion (vol %). This figure depicts the paraffin droplet diameter of the emulsions versus the content of the silica-NH2 NPs at four different paraffin/water ratios. As shown in FIG. 2B, the higher the silica content, the smaller the droplet diameter is at any given volume fractions of the paraffin oil. This is due to the increase of the total surface area of the o/w interface. In addition, under a given content of silica-NH2, the increase of the volume fraction of the paraffin oil results in larger droplet sizes. The diameter of the oil droplets is tunable and can be varied in a relatively wide range of approximately 0.1-300 μm. This shows that the tuning of the emulsion composition allows the fine-tuning of the resulting droplet size, which is important for single cell encapsulation. The relatively high stability of the Pickering emulsion is derived from the low coalescence rate of the droplets due to the presence of the nanoparticles at the interface.

EXAMPLES

The following examples are not meant to limit the scope of the claims in any way. The following examples are put forth so as to provide those of ordinary skill in the art with a complete disclosure and description of how to make and use the described invention, and are not intended to limit the scope of the invention, nor are they intended to represent that the experiments below are all or the only experiments performed. Unless indicated otherwise, parts are parts by weight, molecular weight is weight average molecular weight, temperature is in degrees Centigrade, and pressure is at or near atmospheric.

Example 1—Salinization of Silicon Dioxide Surfaces with APTES

Silica (1 g) (AEROSIL OX 50, with an estimated primary particle size of 40 nm, obtained from Evonik, Germany) was added to 40 mL of methanol and stirred for complete dispersion. Then, APTES (99% Sigma-Aldrich) was added slowly to the solution for a final concentration of 0.5 M. The reaction was carried out at ambient temperature for 45 minutes. After silanization, the particles were collected by centrifugation (9000 rpm for 10 min) and rinsed four times with methanol. Afterward, the silica-NH2 NPs were dried at 35° C. under vacuum for ca. 3 hours.

Example 2—Silica-NH2 Pickering Emulsion Preparation

Pickering emulsions were prepared from amine-functionalized silica in water and paraffin oil (Sigma-Aldrich, analytical grade). First, silica-NH2 NPs were dispersed in distilled water by sonication for 5 min (Sonics Vibra-Cell 750 W, 25% amplitude) with increasing silica content: 0.1, 1, 2, 3, and 5 wt %. Then, paraffin oil was added at the o/w ratios of 5:95, 10:90, 20:80, and 30:70 vol %, respectively. The mixture was sonicated for 5 min for emulsification. FIG. 2A presents confocal microscopy images (a-d) illustrating Pickering emulsions with 1% silica-$NH_2$ at different oil/water ratios. FIG. 2A section (a) demonstrates an oil/water ratio of 5:95. FIG. 2A section (b) demonstrates an oil/water ratio of 10:90. FIG. 2A section (c) demonstrates an oil/water ratio of 20:80. FIG. 2A section (d) demonstrates an oil/water ratio of 30:70. The oil/water ratio can also be: 1:99, 40:60 and 50:50

Example 3—Fungal Strains and Culture Conditions

*M. brunneum* Mb7 and *M. brunneum* Mb7-GFP mutant were cultured on SDA (Difco, Becton-Dickinson, Md.) for 2 weeks at 28° C. until sporulation. Conidial suspensions were prepared by harvesting conidia by scraping the fungal colony, suspending the collected material in sterile distilled water containing 0.01% Triton X-100, followed by vortexing. The suspension was filtered through three layers of gauze, and conidial concentrations were determined using a hemocytometer.

Example 4—Viability Assay

Conidia viability in different suspensions was determined by germination assay. Aliquots of conidial suspension were applied over SDA plates and incubated for 18 h at 28° C. Conidia viability in the emulsion was measured at different time points using confocal microscopy. Conidial fluorescence was the indication for viability as described previously. Viability was satisfactory if rates were above 95% for germination and fluorescent conidia.

Example 5—Conidia Encapsulation in Silica-NH2 Pickering Emulsion

Figure 3A:
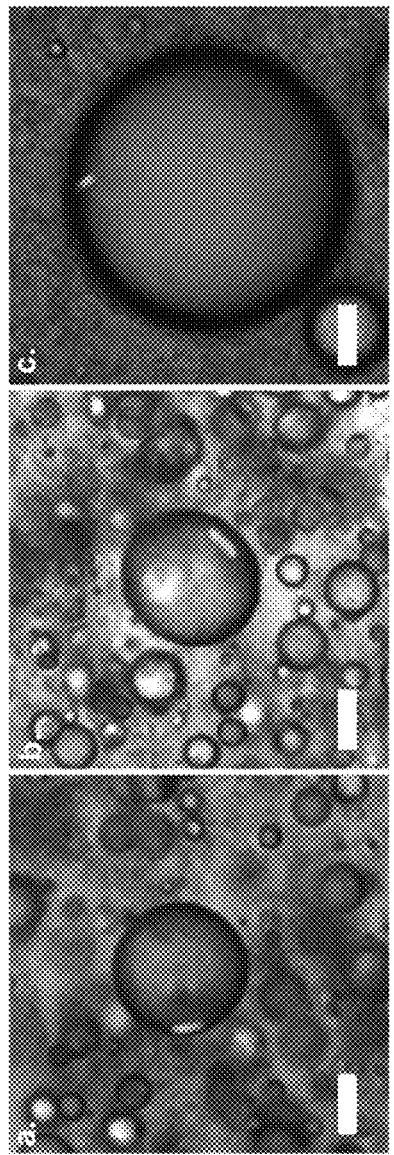
FIG. 3A are confocal microscopy images of single cell encapsulation of *Metarhizium brunneum* Mb7-GFP conidia in a silica-NH2 Pickering emulsion (o/w ratio, 20:80) with different NPs contents of (a) 2 wt %, (b) 3 wt % and (c) 5 wt %. Scale bar is 10 μm.

For single cell encapsulation in the Pickering emulsion, for each of the silica-NH2 NPs content, two different ratios of oil/water were chosen: 20:80 and 30:70. 10 mg of *M. brunneum* Mb7-GFP conidia were added to 10 mL of emulsions. The mixture was vortexed at high speed in vortex mixers for 5 min. Cell samples (10 μL) were placed onto a glass slide and analyzed by confocal microscopy (FIG. 3). The confocal microscopy images are representing one focal plane, thus the conidia cells that appears inside the boundaries of the oil droplets are actually located in the internal part of the paraffin droplets. Successful single cell encapsulation in the paraffin oil droplets was obtained in emulsions with o/w ratio of 20:80 at three different silica contents of 2, 3 and 5 wt % (FIG. 3A). The droplet concentration in these emulsions is approximately an order of magnitude higher than the conidia cell concentration, thus very few droplets that host conidia cells could be detected in a given confocal microscopy image even at very low magnification. FIG. 3A depicts the successful single cell encapsulation of the conidia cells in the paraffin droplets of the emulsions. The Pickering emulsions that have shown successful single cell encapsulation (at silica contents of 2, 3 and 5 wt %) had an average droplet diameter of 9.1±6.8, 4.7±1.7 and 2.7±1.5 μm, respectively (FIG. 2B), close in their values to the size of the conidia cells which are approximately 4 μm in their length. These results indicate that individual encapsulation can be achieved when the sizes of the droplets and the cells are of the same order of magnitude.

The obtained fluorescent signal of the GFP conidia is a clear indication of the viability of the cells when encapsulated in the oil phase of the silica-$NH_2$ Pickering emulsions. The conidia in the emulsions remained viable for three weeks. The viability of the *Metarhizium* conidia cells while encapsulated in the silica-$NH_2$ Pickering emulsions was further characterized by culturing the conidia on a SDA growth medium. The germination percentages of the encapsulated conidia were 85±8.3%, demonstrating their viability and ability to germinate. The control system (without emulsion) had germination percentages of 95±5%.

Figure 3B:
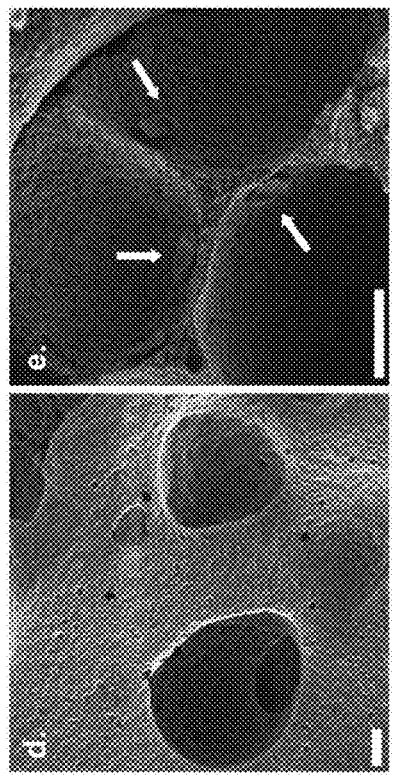
FIG. 3B are SEM micrographs images of dried silica-NH2 Pickering emulsion, (d) without conidia and (e) with conidia (white arrows).

SEM characterization of the applied emulsions revealed a silica based honeycomb structure with ordered hierarchical porosity (FIG. 3B). The white arrows show the conidia particles within the dried silica-NH2 Pickering emulsion. This structure is formed during the drying process of the emulsion through emulsion templating. This finding demonstrates the individual arrangement of the conidia on the leaves, which leads to high efficiency of the biopesticide activity against the target insect.

Figure 4:
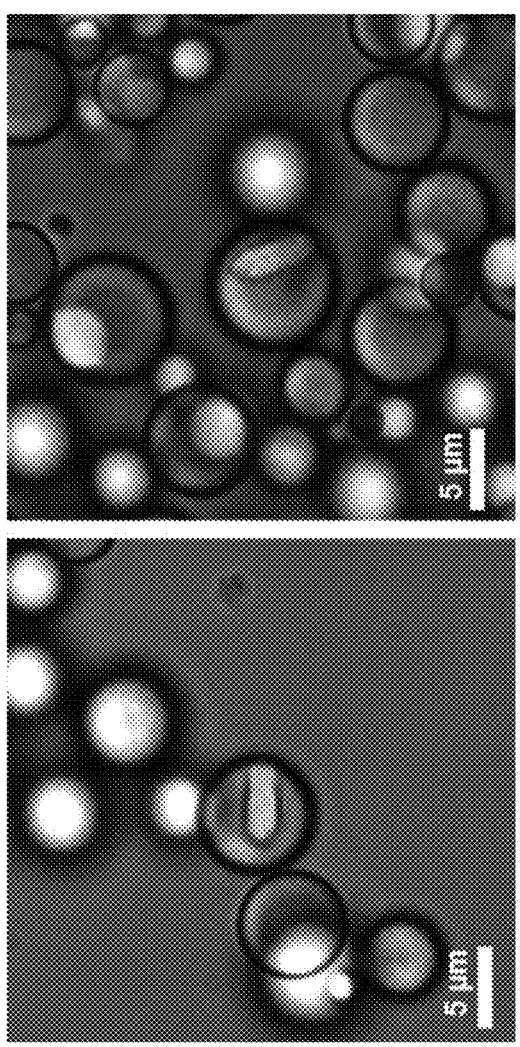
FIG. 4 are confocal microscopy images (a-f) and graph (g) of the distribution of *M. brunneum* Mb7 conidia-GFP on *R. communis* leaves.

Example 6—Conidia Encapsulation in an Oil-in-Water Emulsion Stabilized by Titania Nanoparticles FIG. 4 demonstrates single cell encapsulation of conidia in an oil-in-water emulsion stabilized by Titania nanoparticles. This formulation for biopesticides demonstrates UV protection functionality for the conidia cells due to the UV adsorbing characteristic of the nanoparticles.

Example 7—Conidia Distribution on *R. communis* Leaves

Figure 5:
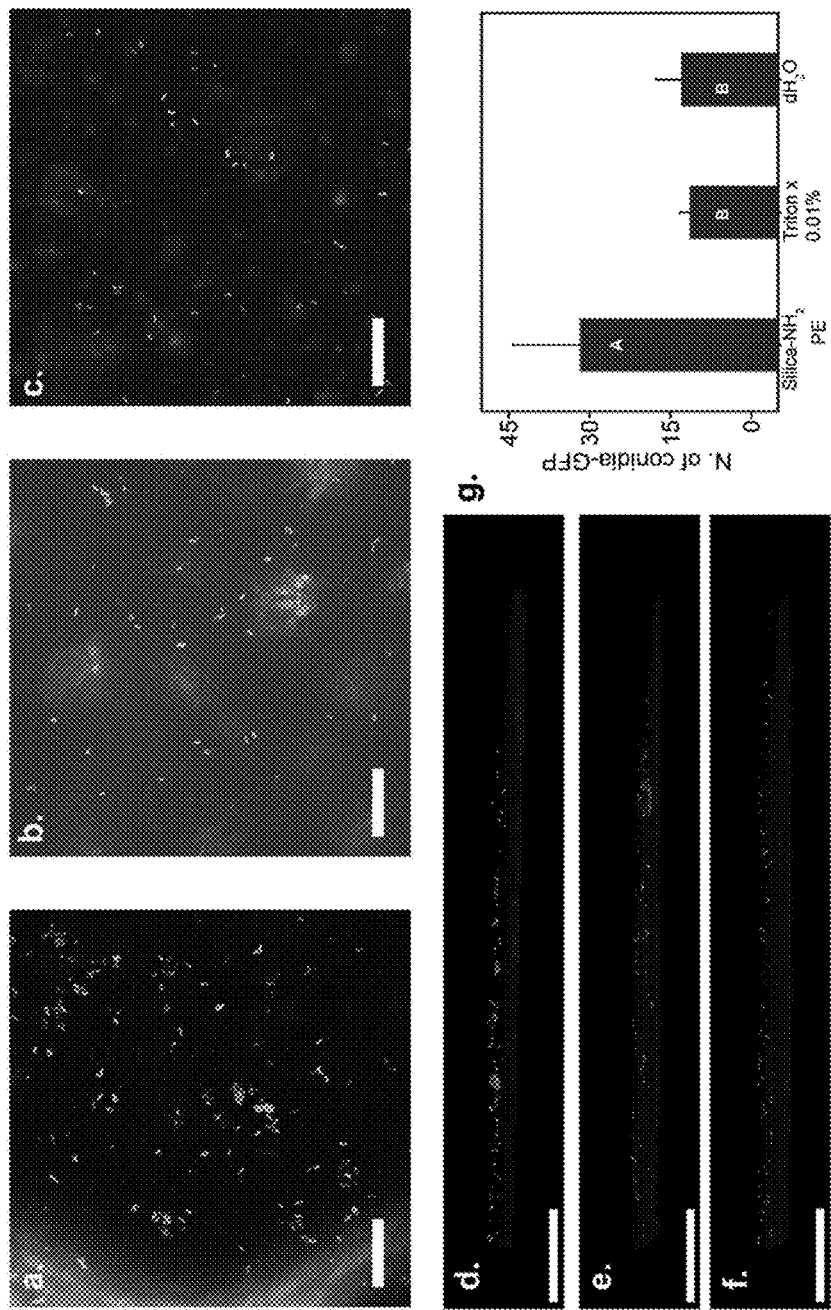
FIG. 5 are confocal microscopy images of single cell encapsulation of conidia in an oil-in-water emulsion stabilized by Titania nanoparticles.

For the leaf spray assays, three conidia samples of *M. brunneum* Mb7-GFP were prepared: silica-NH2 Pickering emulsion, 0.01% Triton X-100, and distilled water. Conidia (10 mg) were added to 10 mL of each sample, mixed well, and then sprayed on *R. communis* leaves using a 50 mL hand sprayer (~100 μL liquid per spray) for full coverage. The plant tissues were left to dry at room temperature. To characterize the distribution of conidia on plant tissues, leaf discs from each treatment were analyzed by confocal microscopy. The distribution of the conidia cells on the leaves was characterized by confocal microscopy. FIG. 5 are confocal microscopy images of the distribution of *M. brunneum* conidia-GFP on *R. communis* leaves. FIG. 5 sections ac are Z projections, while FIG. 5 sections d-f are cross-section views of confocal microscopy images of *M. brunneum*-GFP conidia after spray application on the surface of the leaves. FIG. 5*a* and FIG. 5*d* represent Conidia in silica-NH2 Pickering emulsion, FIG. 5*b* and FIG. 5*e* represent conidia in 0.01% Triton X-100 in water, and FIG. 5*c* and FIG. 5*f* represent conidia in distilled water. FIG. 5*g* represents the Number of conidia on leaves (Students t-test (P=0.05). Scale bar: (a-c) 100 μm (d-f) 200 μm). The silica-NH2 Pickering emulsion (FIG. 5*a,d*) exhibited a significantly higher distribution of conidia cells on the leaves compared to the controls (0.01% Triton X-100, FIG. 5*b,e*; and water, FIG. 5*c,f*). In order to quantify the number of conidia cells on the leaves, a Z series was taken and a Z projection was performed. The results of the Z projection showed a higher count of conidia on the studied system than the controls (FIG. 5*g*, one-way ANOVA: F=4.5042, df=2, P=0.0372). This shows that the single cell encapsulation in the Pickering emulsions maintains the dispersibility of the cells during the spray assay resulting in a higher number of conidia cells on leaves.

Example 8—Biological Functionality of Microencapsulated Conidia as a Biopesticide Formulation To test the functionality of the silica-NH2 Pickering emulsion as a biopesticide formulation, a bioassay was conducted to assess the LT50 of the different samples. *R. communis* leaves were sprayed with Pickering emulsions and controls with and without conidia (see Table 2). Both sides of the *R. communis* leaves were treated using a 50 mL hand sprayer (~100 μL liquid per spray). The suspension contained 10 mL of 10⁸ conidia/mL. After spraying, the leaves were dried for 30 min in a hood. The dried treated leaves were hand cut and inserted into a 55 mm Petri dish lined with filter paper impregnated with 500 μL distilled water to maintain high humidity and a single *S. littoralis* third-instar larva. For each sample, 20 larvae were used. The plates were sealed and incubated at 25° C. under a 12:12 L/D photoperiod. The larvae were examined at days 3, 4, and 7 for mortality (FIGS. 6A and B). Food was supplied during the examination. Dead larvae were removed from the Petri dishes and incubated in a moist chamber until sporulation occurred. The experiment was repeated three times.

TABLE 2

List of samples used in the
biological functionality bioassay

| # | Sample | Conidia presence |
|---|---|---|
| 1 | dH$_2$O | − |
| 2 | 0.01% Triton X-100 | + |
| 3 | Silica-NH$_2$ Pickering emulsion | − |
| 4 | Silica-NH$_2$ Pickering emulsion | + |

Larvae treated with conidia incorporated in the Pickering emulsion showed 75% mortality, whereas the formulation alone resulted in a mortality of only 25%. Treatment with conidia in 0.01% Triton X-100 led to 40% mortality (FIG. 6A). Corrected mortality and probability tests were performed on the data. The analysis of corrected mortality is based on Abbott's formula which is the adjustment of insect mortality rates used worldwide in insecticide trials. The results are presented in FIG. 6B and Table 3, respectively.

TABLE 3

Median lethal time in days (LT50) of the treatments in the
*Spodoptera litorallis* larvae assay

| Type | Conidia | LT50 | lower 95% | upper 95% | Prob > ChiSq |
|---|---|---|---|---|---|
| dH$_2$O | − | 11.48 | 7.94 | — | — |
| 0.01% Triton X 100 | + | 8.25 | 6.99 | 13.77 | 0.5594 |
| Silica-NH$_2$ Pickering emulsion | − | 16.97 | 8.8 | — | <0.001 |
| Silica-NH$_2$ Pickering emulsion | + | 4.89 | 4.23 | 5.69 | <0.013 |

Table 3 shows the higher pesticidal activity of conidia incorporated in the Pickering emulsions compared to the controls. The sporulation processes started seven days post-inoculation. The dead larvae were kept separately under moist conditions to promote sporulation and confirm mycosis. Cadavers were monitored daily for sporulation. Of the 14 dead larvae, 13 were mycosed. A sporulated larva cadaver is presented in FIG. 7A, while untreated larva from the control group is shown in FIG. 7B.

Example 9—Confocal Laser Scanning Microscopy and Image Analysis

The samples were analyzed by laser scanning confocal microscopy (Olympus, FluoView 500) using argon laser 488 nm excitation. Fluorescence emission of GFP was recorded at 500-520 nm. For 3D images, acquisition used a Leica SP8 laser scanning microscope (Leica, Wetzlar, Germany) equipped with a solid state laser with 488 nm light, HC PL APO CS 20×/0.75 objective (Leica, Wetzlar, Germany) and Leica Application Suite X software (LAS X, Leica, Wetzlar, Germany). Imaging of the GFP signal was done using the argon laser, and the emission was detected in a range of 500-525 nm. Autofluorescence of the chloroplasts was detected in a range of 650-700 nm. For *M. brunneum* Mb7-GFP conidia counting, image stacks were first projected using a Z projection (as maximum intensity) to find all the fluorescent conidia, then counted by a cell counter using Fiji software. The droplet average diameter was measured for every sample by the particles analysis tool of Fiji software based on confocal microscopy images. 12 droplets were sampled from each image and plotted as a 3D graph with Origin (OriginLab, Northampton, Mass.).

Example 10—Scanning Electron Microscopy

SEM measurements were performed using a MIRA3 field-emission SEM microscope (TESCAN, Brno/Czech Republic) with an acceleration voltage of 1.0 kV and a secondary electron detector. Pickering emulsion samples were drop-cast on a conductive double stick carbon tape and dried under ambient conditions. Prior to imaging, a thin layer of carbon was evaporated onto them to render them electrically conductive and to avoid surface charging by the electron beam.

While the invention has been described with respect to a limited number of embodiments, it will be appreciated that many variations, modifications and other applications of the invention may be made. Therefore, the claimed invention as recited in the claims that follow is not limited to the embodiments described herein.

The invention claimed is:

1. A method for single cell encapsulation comprising:
providing a water-based solution including amine functionalized silica nanoparticles;
emulsifying the water-based solution by adding an oil solution into the water-based solution to form oil-in-water Pickering emulsions;
adding cells of *Metarhizium* spore into said solution containing the oil-in-water Pickering emulsions;
generating at least one single cell encapsulation of the cells by vortexing, wherein the content of the nanoparticles is between 0.1 wt % to 10 wt %, and the oil/water ratio is one of: 1:99, 5:95, 10:90, 20:80, 30:70, 40:60 and 50:50 respectively.

2. The method of claim 1, wherein said oil-based solution is one of: paraffin oil, silicone oil, sunflower oil, and mineral oil.

3. The method of claim 1, wherein said *Metarhizium* is one of *Metarhizium anisopliae, Metarhizium brunneum, Metarhizium robertsii, Metarhizium frigidum, Metarhizium riley, Metarhizium acridum*.

4. The method of claim 3 wherein said *Metarhizium brunneum* is *Metarhizium brunneum* Mb7.

5. The method of claim 1, wherein said nanoparticles are functionalized with silane selected from the group consisting of: Acryloxymethyltrimethoxysilane, (3-acryloxypropyl) trimethoxysilane, 3-aminopropyltrimethoxysilane, 3-aminopropyltriethoxysilane, n-(2-aminoethyl)-3-aminopropyltrimethoxysilane, Ethyltrimethoxysilane, n-propyltriethoxysilane, Isobutyltriethoxysilane, Hexyltrimethoxysilane, Octyltrimethoxysilane, 4-Aminobutyltriethoxysilane, 3-Aminopropyldiisopropylethoxysilane, 3-Mercaptopropyltriethoxysilane, 3-Mercaptopropyltrimethoxysilane, 1-Mercaptoundecyltrimethoxysilane, S-(Octanoyl)Mercaptopropyltriethoxysilane, 1H,1H,2H,2H-Perfluorooctyltrimethoxysilane, (3,3,3-Trifluoropropyl) trimethoxysilane, n-Octylmethyldiethoxysilane, (3,3,3-trifluoropropyl) trimethoxysilane, Undecyltrichlorosilane, Dodecyltriethoxysilane, Docosyltriethoxysilane, Dimethyldimethoxysilane, Dimethyldichlorosilane, n-Butyltriethoxysilane, (3-glycidyloxypropyl)trimethoxysilane, 2-(3,4-epoxycyclohexyl)ethyltrimethoxysilane, 3-isocyanatopropyltriethoxysilane, bis[3-(triethoxysilyl)propyl]tetrasulfide.

6. A method for pest control comprising:
(i) generating the emulsion comprising encapsulated single cells according to the method defined in any one of the preceding claims and;
(ii) applying the emulsion onto at least one leaf.

7. The method of claim 6, wherein said at least one leaf is a *R. communis* Leaf.

* * * * *